(12) United States Patent
Huang (10) Patent No.: US 10,330,645 B2
(45) Date of Patent: Jun. 25, 2019

(54) SYSTEMS AND METHODS FOR DETERMINING CRACK PROPAGATION LENGTH INSIDE A STRUCTURE USING A TECHNIQUE BASED ON ACOUSTIC SIGNATURE

(71) Applicant: Livermore Software Technology Corporation, Livermore, CA (US)

(72) Inventor: Yun Huang, Dublin, CA (US)

(73) Assignee: Livermore Software Tecchnology Corp., Livermore, CA (US)

(*) Notice: Subject to any disclaimer, the term of this patent is extended or adjusted under 35 U.S.C. 154(b) by 302 days.

(21) Appl. No.: 15/263,891

(22) Filed: Sep. 13, 2016

(65) Prior Publication Data

US 2018/0074022 A1   Mar. 15, 2018

(51) Int. Cl.

| | |
|---|---|
| *G01N 29/12* | (2006.01) |
| *G01N 29/44* | (2006.01) |
| *G01N 29/04* | (2006.01) |
| *G01N 29/07* | (2006.01) |
| *G01N 29/34* | (2006.01) |
| *G01N 29/46* | (2006.01) |

(52) U.S. Cl.
CPC .......... *G01N 29/12* (2013.01); *G01N 29/045* (2013.01); *G01N 29/07* (2013.01); *G01N 29/348* (2013.01); *G01N 29/44* (2013.01); *G01N 29/4427* (2013.01); *G01N 29/4454* (2013.01); *G01N 29/46* (2013.01)

(58) Field of Classification Search
CPC .... G01N 29/12; G01N 29/46; G01N 29/4454; G01N 29/4427; G01N 29/07; G01N 29/045; G01N 29/44; G01N 29/348

USPC .......................................................... 703/7
See application file for complete search history.

(56) References Cited

U.S. PATENT DOCUMENTS 3,924,456 A * 12/1975 Vahaviolos .............. G01H 1/00
                                                              73/587

* cited by examiner

*Primary Examiner* — Saif A Alhija
(74) *Attorney, Agent, or Firm* — Roger H. Chu (57) ABSTRACT

Methods and systems for determining crack propagation length using a technique based on acoustic signature are disclosed. An acoustic signature is measured and recorded at a first location via acoustic wave generated by structural vibrations caused by a harmonic loading with predefined magnitude acted at a second location on the structure. Structure contains an unknown length of crack propagation inside. Unknown length is determined by comparing the measured and recorded acoustic signature with numerically-computed acoustic signatures stored in a database, which contains at least one relationship of the numerically-computed acoustic signatures versus respective crack propagation lengths at various stages of numerically-simulated crack propagation trajectory. Numerically-computed acoustic signatures are obtained by conducting a numerical time-marching simulation for obtaining a numerically-simulated crack propagation trajectory, and by conducting a SSD analysis and a vibro-acoustic analysis of the structure for obtaining the numerically-computed acoustic signatures at various stages of the numerically-simulated crack propagation trajectory.

18 Claims, 7 Drawing Sheets

100

102
Measure and record an acoustic signature at a first location via acoustic wave generated by vibrations of a structure caused by a harmonic loading acted at a second location on the structure, the structure containing an unknown length of crack propagation inside

104
Determine the unknown length of crack propagation inside the structure by comparing the measured acoustic signature with prior computed acoustic signatures stored in a database, the database contains at least one relationship of numerically-computed acoustic signatures versus respective crack propagation lengths at various stages of crack propagation trajectory, wherein the numerically-computed acoustic signatures are obtained by conducting a numerical time-marching simulation for obtaining a numerically-simulated crack propagation trajectory, and conducting a steady-state dynamic (SSD) analysis and a vibro-acoustic analysis of the structure for obtaining the numerically-computed acoustic signatures at said various stages of the numerically-simulated crack propagation trajectory

SYSTEMS AND METHODS FOR DETERMINING CRACK PROPAGATION LENGTH INSIDE A STRUCTURE USING A TECHNIQUE BASED ON ACOUSTIC SIGNATURE

FIELD

The invention generally relates to determination of crack propagation length within a structure, more particularly to systems and methods of determining crack propagation length inside a structure using a technique based on acoustic signature (e.g., acoustic frequency response function).

BACKGROUND

It is well known that a structure may develop crack under cyclic loading. Sources of the cyclic loading can come from normal operation or vibrations during transportation. Once a crack is initially developed, the crack may propagate due to a number of possible factors, including but not limited to, continued operational loading, combined effect from environment and or temperature, etc. In certain extreme situations, the crack can propagate so much to cause structural failure. Therefore, it is vitally important to monitor the development and propagation of cracks in a structure to ensure that the structural integrity is maintained.

With advent of various engineering disciplines, there are several techniques that can assist a user (i.e., scientists, engineers, etc.) to perform this difficult determination. For example, Computer Aided Engineering (CAE) has been used for supporting engineers in many tasks, particularly CAE (e.g., finite element method, boundary element method, meshfree method, etc.) can be used for obtaining numerically simulated structural behaviors (e.g., crack propagations) in a time-marching simulation of structure under a cyclic loading.

FEA is a computerized method widely used in industry to simulate (i.e., model and solve) engineering problems relating to complex products or systems (e.g., cars, airplanes, etc.) such as three-dimensional linear and/or non-linear structural design and analysis. FEA derives its name from the manner in which the geometry of the object under consideration is specified. The geometry is defined by elements and nodes. There are many types of elements, for example, solid elements for volumes or continua, shell or plate elements for surfaces and beam or truss elements for one-dimensional structure objects.

However, it is generally difficult to physically determine or measure the length of a crack especially when the crack propagates inwards within a structure.

SUMMARY

This section is for the purpose of summarizing some aspects of the invention and to briefly introduce some preferred embodiments. Simplifications or omissions in this section as well as in the abstract and the title herein may be made to avoid obscuring the purpose of the section. Such simplifications or omissions are not intended to limit the scope of the invention.

Methods and systems for determining crack propagation length using a technique based on acoustic signature are disclosed. According to one example aspect, a method of determining an unknown length of crack propagation inside a structure comprises measuring and recording an acoustic signature at a first location via acoustic wave generated by vibrations of a structure caused by a harmonic loading with predefined magnitude acted at a second location on the structure. Structure contains an unknown length of crack propagation inside. Unknown length is determined by comparing the measured and recorded acoustic signature with numerically-computed acoustic signatures stored in a database, which contains at least one relationship of the numerically-computed acoustic signatures versus respective crack propagation lengths at various stages of numerically-simulated crack propagation trajectory. Numerically-computed acoustic signatures are obtained by conducting a numerical time-marching simulation for obtaining a numerically-simulated crack propagation trajectory, and by conducting a steady-state dynamic (SSD) analysis and a vibro-acoustic analysis of the structure for obtaining the numerically-computed acoustic signatures at various stages of the numerically-simulated crack propagation trajectory.

According to another aspect, conducting the numerical time-marching simulation for obtaining the numerically-simulated crack propagation trajectory further comprises the following operations: receiving, in a computer system having at least a finite element analysis (FEA) application module and a boundary element method (BEM) application module installed thereon, a FEA model representing the structure and a loading condition known to cause a crack propagation in the structure; and obtaining, with the FEA application module, the numerically-simulated crack propagation trajectory within the structure under the loading condition by conducting the time-marching simulation using the FEA model based on at least one structural crack prediction theory.

According to yet another aspect, conducting the steady-state dynamic (SSD) analysis and the vibro-acoustic analysis of the structure for obtaining the numerically-computed acoustic signatures at various stages of the numerically-simulated crack propagation trajectory further comprises the following steps: obtaining, with the FEA application module's SSD analysis capability, a structural surface nodal velocity distribution of the structure subject to a harmonic loading with predefined magnitude at a predefined frequency acted on a sound generation location on the structure's surface, the structure is represented by the FEA model corresponding to each of the various stages of the numerically-simulated crack propagation trajectory; and obtaining, with the BEM application module, the numerically-computed acoustic signatures of the structure at a sound receiving location using the structural surface nodal velocity distribution as a vibration boundary condition based on a vibro-acoustic computation theory.

Objects, features, and advantages of the invention will become apparent upon examining the following detailed description of an embodiment thereof, taken in conjunction with the attached drawings.

BRIEF DESCRIPTION OF THE DRAWINGS

These and other features, aspects, and advantages of the invention will be better understood with regard to the following description, appended claims, and accompanying drawings as follows:

DETAILED DESCRIPTIONS

In the following description, numerous specific details are set forth in order to provide a thorough understanding of the invention. However, it will become obvious to those skilled in the art that the invention may be practiced without these specific details. The descriptions and representations herein are the common means used by those experienced or skilled in the art to most effectively convey the substance of their work to others skilled in the art. In other instances, well-known methods, procedures, and components have not been described in detail to avoid unnecessarily obscuring aspects of the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the invention are discussed herein with reference to FIGS. 1A-6. However, those skilled in the art will readily appreciate that the detailed description given herein with respect to these figures is for explanatory purposes as the invention extends beyond these limited embodiments.

Figure 1A:
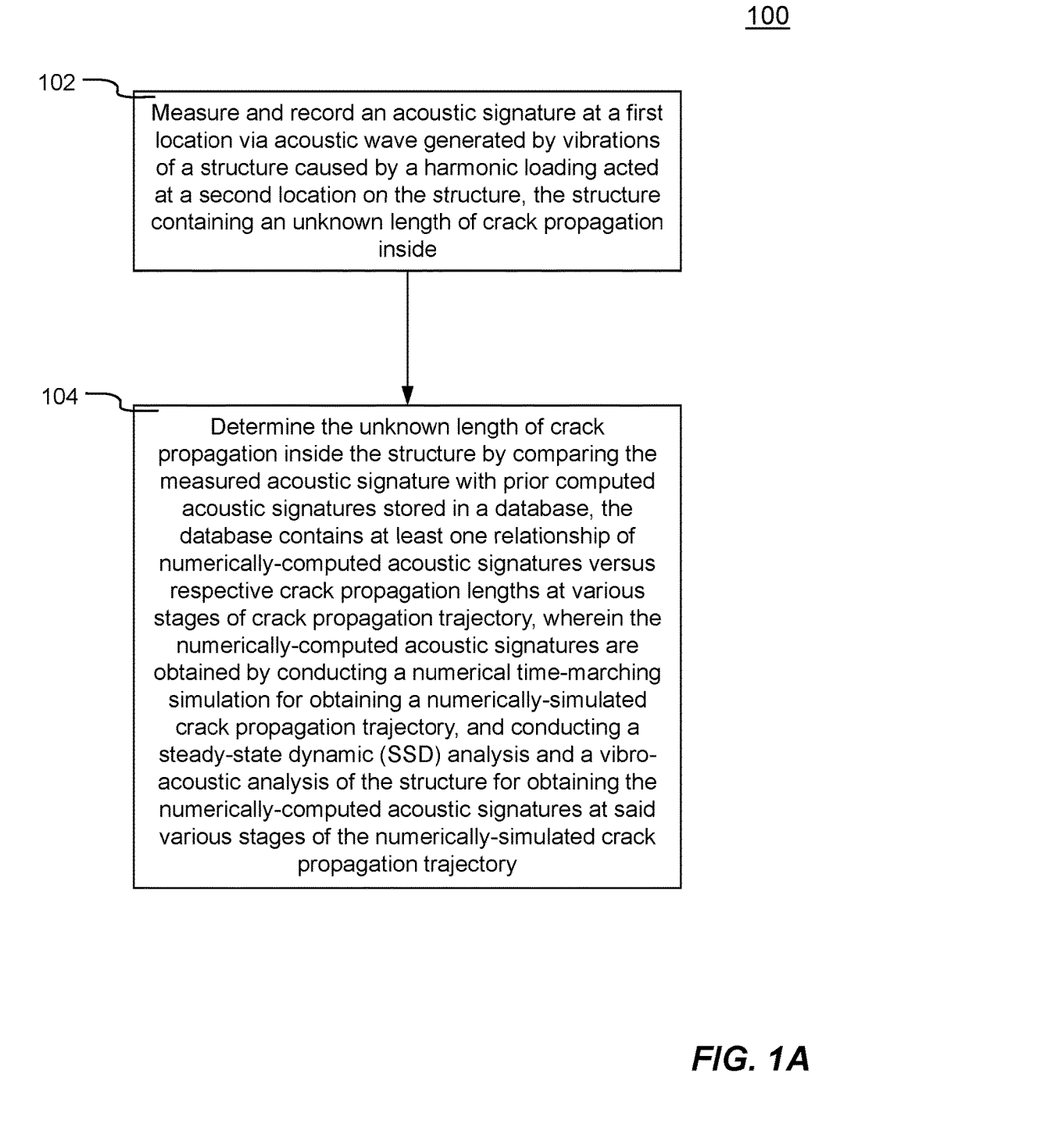
FIG. 1A is a flowchart illustrating an example process of determining unknown crack propagation length inside a structure using a technique based on acoustic signature, according to one embodiment of the invention.

Referring first to FIG. 1A, it is shown a flowchart illustrating an example process 100 of unknown length of crack propagation inside a structure using a technique based on acoustic signature. Process 100 starts at action 102 by measuring and recording an acoustic signature at a first location (i.e., sound receiving location) via acoustic/sound wave generated by vibrations of a structure. The structure contains an unknown length of crack propagation inside the structure. The vibrations of the structure are caused by a harmonic loading (e.g., sinusoidal loads at certain frequency) with predefined magnitude applied on a second location (i.e., sound generation location) on the structure. In one embodiment, the first location is near the structure or within the characteristic dimension of the structure (e.g., largest dimension of the structure, average dimension, etc.), while the second location is on the surface of the structure. The largest dimension may be the largest dimension between two extreme locations of the structure. In another embodiment, the predefined magnitude and predefined frequency of the harmonic loading cause the acoustic signature recorded at the sound receiving location an audible sound (e.g., at least 30 dB).

Figure 2:
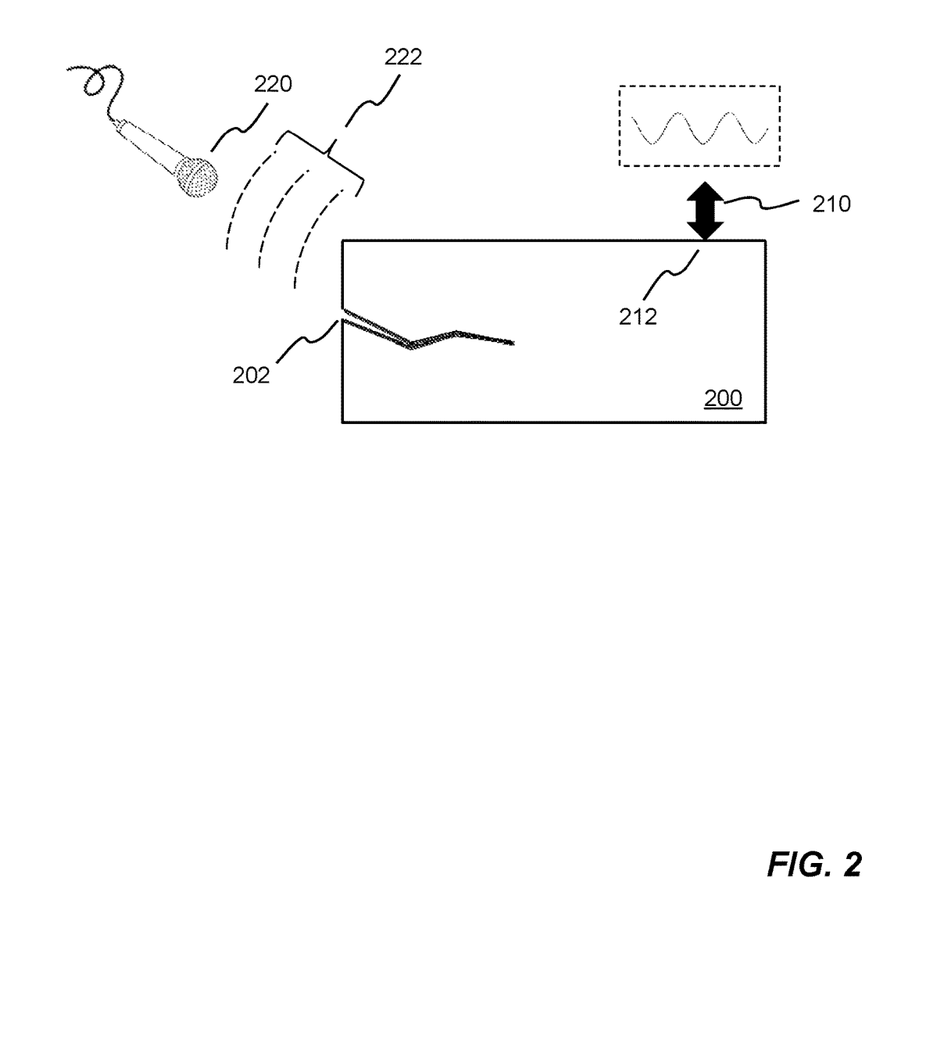
FIG. 2 is a diagram showing an example measurement set up of acoustic signature generated by an example structure under a harmonic loading with predefined magnitude, according to one embodiment of the invention.

FIG. 2 shows an example setup of such a measurement. An example structure 200 having a crack propagation 202 subjected to a harmonic loading with predefined magnitude 210 at a second location 212 (e.g., location of external harmonic loading). Acoustic signature via sound wave 222 is measured and recorded at a first location 220 (e.g., location of a microphone) near the structure 200. For illustration simplicity, a two-dimensional view of the structure 200 is shown. There is no limit as to what types of structure in the invention. Structures can be 1-, 2- or 3-dimensional, can be any shape. Structures can also be made of any material, for example, metal, concrete, etc. Measurement and recording of the acoustic signatures can be made with a number of well-known techniques, for example, acoustic (sound) pressure is measured in terms of Pa (Pascals) or SPL (sound pressure level) in dB (decibels). In an alternative embodiment, the measurement can be an audio file (e.g., a WAV file containing the sound carried in the sound wave). The harmonic loading can be generated by well known methods and systems.

At action 104, the unknown length of the crack propagation within the structure is determined by comparing the measured and recorded acoustic signature with numerically-computed acoustic signatures stored in a database. The database contains at least one relationship of numerically-computed acoustic signatures versus respective crack propagation lengths at various stages of numerically-simulated crack propagation trajectory. The numerically-computed acoustic signatures are obtained by conducting a numerical time-marching simulation for obtaining a numerically-simulated crack propagation trajectory, and by conducting a steady-state dynamic (SSD) analysis and a vibro-acoustic analysis of the structure for obtaining the numerically-computed acoustic signatures at various stages of the numerically-simulated crack propagation trajectory. More details are described and shown in FIG. 1B, in which a flowchart illustrates an example process 150 of creating a database of numerically-computed acoustic signature versus crack propagation length of a structure subject to a harmonic loading with the structure contains a crack propagation inside. The determination can be done with many well-known procedures, for example, interpolation of the computed acoustic signatures.

Figure 1B:
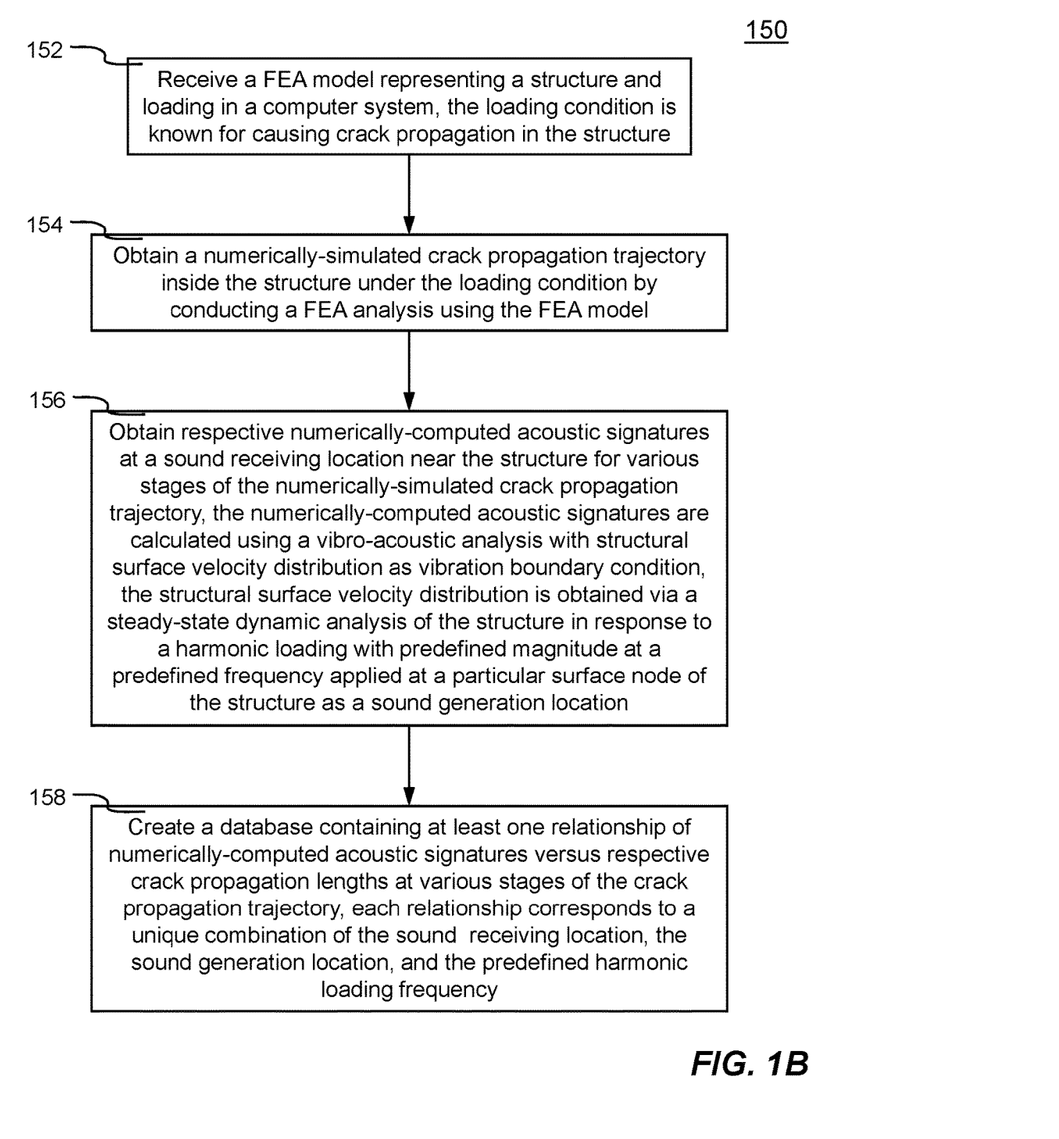
FIG. 1B is a flowchart illustrating an example process of creating a database of numerically-computed acoustic signatures at a location near a structure having various lengths of crack propagation under a harmonic loading with predefined magnitude, according to one embodiment of the invention.

Process 150 is preferably implemented in software and understood with other figures. Process 150 starts at action 152 by receiving a finite element analysis (FEA) model representing a structure and a loading condition in a computer system (e.g., computer system 600 of FIG. 6). The loading condition is known to cause crack propagation in the structure. The computer system has at least a finite element analysis (FEA) application module and a boundary element method (BEM) application module installed thereon. Prediction of crack propagation and SSD analysis are functions/features of the FEA application module, while vibro-acoustic analysis is of the BEM application module.

At action 154, a numerical time-marching simulation (e.g., finite element analysis) is conducted to obtain a numerically-simulated crack propagation trajectory within the structure under the loading condition using the FEA model. There are several well known procedures to predict the crack propagation, for example, the ones based on strain energy release theory, or stress intensity factor (SIF), or cohesive zone modeling, etc. Those having ordinary skill in the art would know that the numerical simulation can be used for predicting crack propagation with high degree of confidence.

At action 156, respective numerically-computed acoustic signatures are obtained at a sound receiving location near the structure for various stages of the numerically-simulated crack propagation trajectory. Each stage corresponds to a specific length of the numerical-simulated crack propagation trajectory, for example, three example stages shown in FIG. 3. The computed acoustic signatures are calculated using a vibro-acoustic analysis based on boundary element method with structural surface velocity distribution as vibration boundary condition. The structural surface velocity distribution is obtained via a steady-state dynamic (SSD) analysis of the structure in response to a harmonic loading with predefined magnitude at a predefined frequency (e.g., defined by a user). The harmonic loading is applied at a particular surface node of the structure (i.e., the sound generation location). SSD is performed in frequency domain, and can be conducted by two methods: direct SSD and mode-based SSD (which is also called as indirect SSD). For direct SSD, the variables are the physical nodal coordinates. While for mode-based SSD, the variables are the modal coordinates or generalized coordinates. Both of the SSD approaches are well-known.

Figure 3:
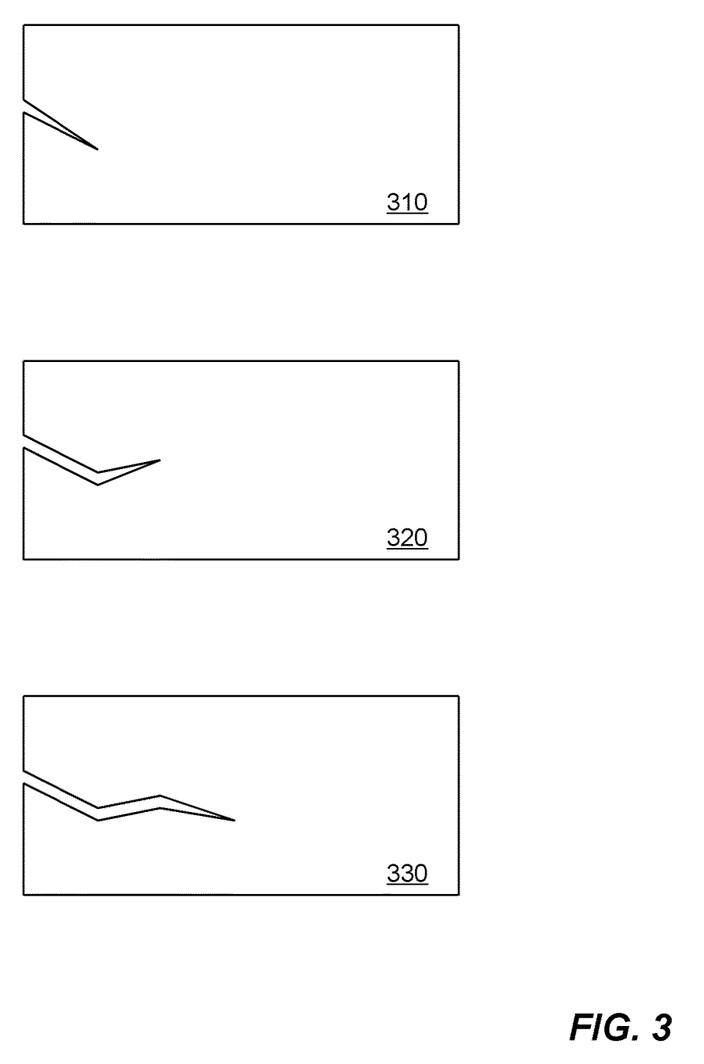
FIG. 3 is a series of diagrams showing various stages of crack propagation inside an example structure, according to an embodiment of the invention.

FIG. 3 illustrates three stages of crack propagation within an example structure. Stage-1 310 and stage-2 320 represent intermittent stages, while stage-3 330 represents the final stage or the entire numerically-simulated crack propagation trajectory. The crack is drawn as exaggeratedly-enlarged gap for visual and illustration purpose. In reality, not only the crack may be much smaller/thinner, the crack could also be hidden within the structure (may not be visible from outside). In one embodiment, the acoustic signature is computed for each stage of the numerically-simulated crack propagation trajectory.

Figure 4:
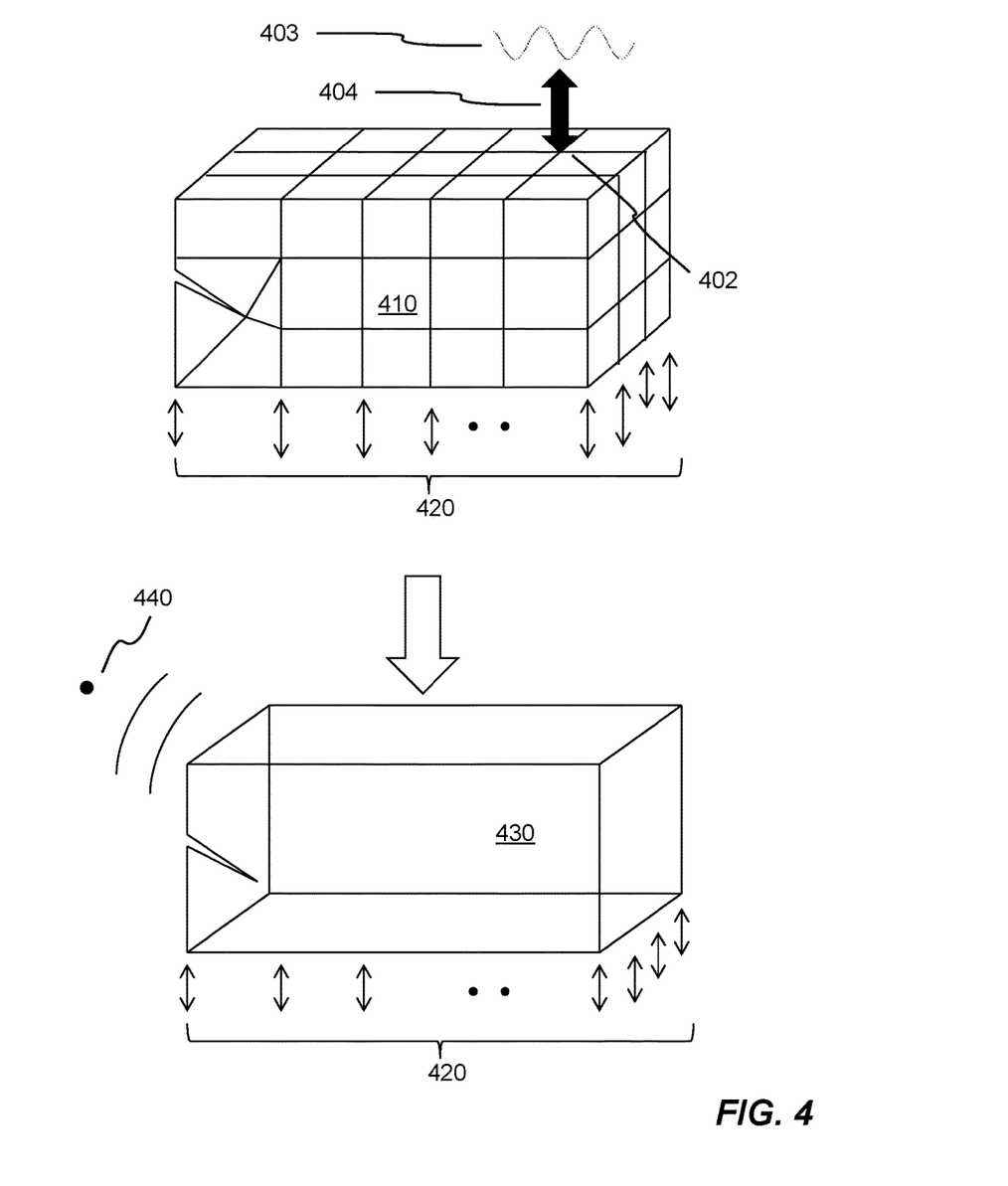
FIG. 4 is a diagram illustrating an example scheme to obtain numerically-computed acoustic signatures of a structure at a particular stage of crack propagation trajectory, according to one embodiment of the invention.

FIG. 4 shows an example scheme to obtain numerically-computed acoustic signatures of a structure at a particular stage of numerically-simulated crack propagation trajectory. The scheme contains two phases: 1) using SSD analysis to obtain numerical structural surface velocity distribution in response to a harmonic loading with predefined magnitude; and 2) using vibro-acoustic analysis to obtain the acoustic signature of the structure due to structure vibration represented by the structural surface velocity distribution.

A finite element analysis model 410 of the structure at a particular stage of numerically-simulated crack propagation trajectory (e.g., stage-1 310 of FIG. 3). A harmonic loading with predefined magnitude 404 is applied at a surface node 402 (i.e., sound generation location). The harmonic loading has a predefined frequency 403 (e.g., a sinusoidal wave with a particular frequency). Structural surface nodal velocity distribution 420 can be computed via the SSD analysis. The structural surface nodal velocity distribution 420 is then used as vibration boundary condition in boundary element method using structural surface model 430. Acoustic signature can be computed at a sound receiving location 440. It is noted that the structural surface nodal velocity distribution 420 is generally different for each node in terms of amplitude and phase.

Referring back to process 150, at action 158, a database of computed acoustic signatures is created. The database contains at least one relationship of computed acoustic signatures versus respective crack propagation lengths at various stages of the numerically-simulated crack propagation trajectory. Each relationship corresponds to a unique combination of a sound receiving location, a sound generation location and a predefined harmonic loading frequency.

Figure 5:
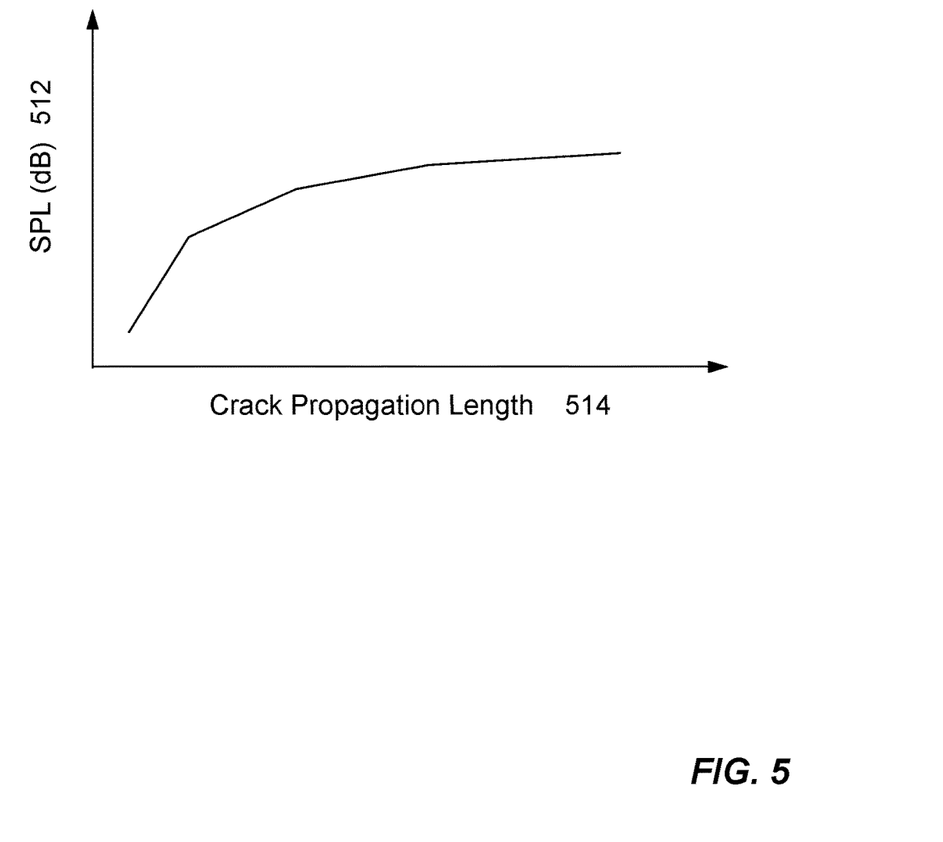
FIG. 5 is a diagram showing an example relationship of numerically-computed acoustic signatures versus respective crack propagation lengths, according to one embodiment of the invention.

FIG. 5 shows such an example relationship of numerically-computed acoustic signatures (i.e., SPL (dB)) 512 and respective crack propagation lengths 514. It is noted that the numerically-computed acoustic signature can be audio file (WAV file) for each stage of numerically-simulated crack propagation trajectory.

Figure 6:
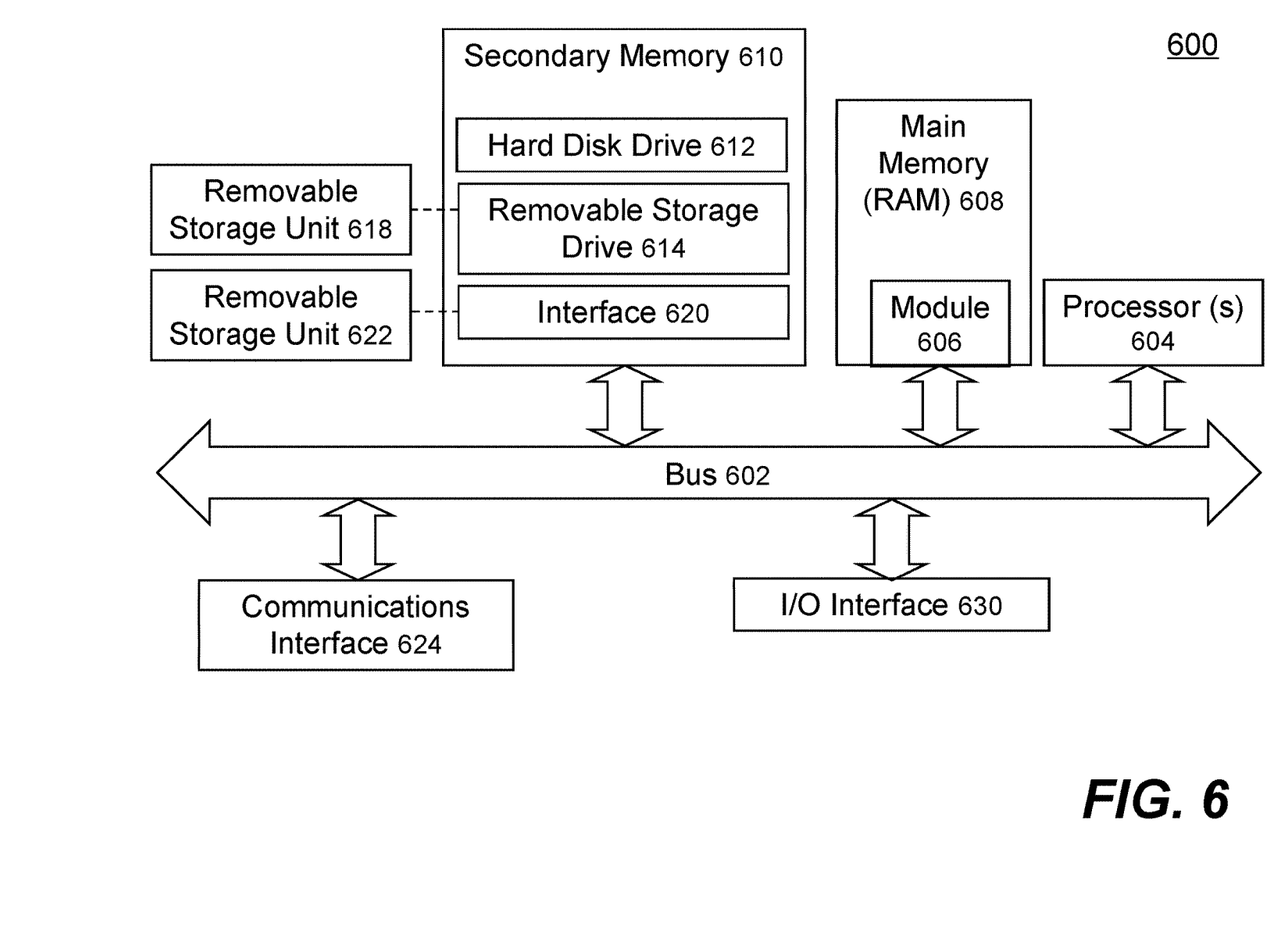
FIG. 6 is a function block diagram showing salient components of an example computer system, in which one embodiment of the invention may be implemented.

According to another aspect, the invention is directed towards one or more computer systems capable of carrying out the functionality described herein. An example of a computer system 600 is shown in FIG. 6. The computer system 600 includes one or more processors, such as processor 604. The processor 604 is connected to a computer system internal communication bus 602. Various software embodiments are described in terms of this exemplary computer system. After reading this description, it will become apparent to a person skilled in the relevant art(s) how to implement the invention using other computer systems and/or computer architectures.

Computer system 600 also includes a main memory 608, preferably random access memory (RAM), and may also include a secondary memory 610. The secondary memory 610 may include, for example, one or more hard disk drives 612 and/or one or more removable storage drives 614, representing a floppy disk drive, a magnetic tape drive, an optical disk drive, etc. The removable storage drive 614 reads from and/or writes to a removable storage unit 618 in a well-known manner. Removable storage unit 618, represents a flash memory, floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other similar means for allowing computer programs or other instructions to be loaded into computer system 600. Such means may include, for example, a removable storage unit 622 and an interface 620. Examples of such may include a program cartridge and cartridge interface (such as that found in video game devices), a removable memory chip (such as Erasable Programmable Read-Only Memory (EPROM), Universal Serial Bus (USB) flash memory, or PROM) and associated socket, and other removable storage units 622 and interfaces 620 which allow software and data to be transferred from the removable storage unit 622 to computer system 600. In general, Computer system 600 is controlled and coordinated by operating system (OS) software, which performs tasks such as process scheduling, memory management, networking and I/O services.

There may also be a communications interface 624 connecting to the bus 602. Communications interface 624 allows software and data to be transferred between computer system 600 and external devices. Examples of communications interface 624 may include a modem, a network interface (such as an Ethernet card), a communications port, a PCMCIA slot and card, etc.

The computer 600 communicates with other computing devices over a data network based on a special set of rules (i.e., a protocol) to send data back and forth. One of the common protocols is TCP/IP (Transmission Control Protocol/Internet Protocol) commonly used in the Internet. In general, the communication interface 624 manages the assembling of a data file into smaller packets that are transmitted over the data network or reassembles received packets into the original data file. In addition, the communication interface 624 handles the address part of each packet so that it gets to the right destination or intercepts packets destined for the computer 600.

In this document, the terms "computer recordable storage medium", "computer recordable medium" and "computer readable medium" are used to generally refer to media such as removable storage drive 614, and/or a hard disk installed in hard disk drive 612. These computer program products are means for providing software to computer system 600. The invention is directed to such computer program products.

The computer system 600 may also include an I/O interface 630, which provides the computer system 600 to access monitor, keyboard, mouse, printer, scanner, plotter, and alike.

Computer programs (also called computer control logic) are stored as application modules 606 in main memory 608 and/or secondary memory 610. Computer programs may also be received via communications interface 624. Such computer programs, when executed, enable the computer system 600 to perform the features of the invention as discussed herein. In particular, the computer programs, when executed, enable the processor 604 to perform features of the invention. Accordingly, such computer programs represent controllers of the computer system 600.

In an embodiment where the invention is implemented using software, the software may be stored in a computer program product and loaded into computer system 600 using removable storage drives 614, hard drive 612, or communications interface 624. The application module 606, when executed by the processor 604, causes the processor 604 to perform the functions of the invention as described herein.

The main memory 608 may be loaded with one or more application modules 606 that can be executed by one or more processors 604 with or without a user input through the I/O interface 630 to achieve desired tasks. In operation, when at least one processor 604 executes one of the application modules 606, the results (e.g., SSD results—structural surface nodal velocity distribution, acoustic signature database) are computed and stored in the secondary memory 610 (i.e., hard disk drive 612). For example, the SSD results can be saved to memory and reported to the user via the I/O interface 630 either as a list or a graph.

Although the invention has been described with reference to specific embodiments thereof, these embodiments are merely illustrative, and not restrictive of, the invention. Various modifications or changes to the specifically disclosed exemplary embodiments will be suggested to persons skilled in the art. For example, whereas the structure has been shown as rectangular two-dimensional shape, other types or shapes may be used in the invention, for example, three-dimensional complex structure such as an automobile or a component of an automobile. In summary, the scope of the invention should not be restricted to the specific exemplary embodiments disclosed herein, and all modifications that are readily suggested to those of ordinary skill in the art should be included within the spirit and purview of this application and scope of the appended claims.

I claim:

1. A method of determining an unknown length of crack propagation inside a structure comprising:
    measuring and recording an acoustic signature at a first location via acoustic wave generated by vibrations of a structure caused by a harmonic loading with a predefined magnitude acted at a second location on the structure, the structure containing an unknown length of crack propagation inside;
    creating a database that contains at least one relationship of numerically computed acoustic signatures versus respective crack propagation lengths at various stages along a numerically-simulated crack propagation trajectory obtained in a numerical time-marching simulation of the structure;
    obtaining the numerically-computed acoustic signatures by conducting a steady-state dynamic (SSD) analysis and a vibro-acoustic analysis of the structure at the various stages of the numerically-simulated crack propagation trajectory; and
    determining the unknown length of crack propagation within the structure by comparing the measured and recorded acoustic signature with the numerically-computed acoustic signatures stored in the database.

2. The method of claim 1, wherein the first location comprises a sound receiving location that is located within a characteristic dimension of the structure.

3. The method of claim 1, wherein the second location comprises a sound generation location on the surface of the structure.

4. The method of claim 1, said conducting the numerical time-marching simulation further comprises:
    receiving, in a computer system having at least a finite element analysis (FEA) application module and a boundary element method (BEM) application module installed thereon, a FEA model representing the structure and a loading condition known to cause a crack propagation in the structure; and
    obtaining, with the FEA application module, the numerically-simulated crack propagation trajectory within the structure under the loading condition by conducting the time-marching simulation using the FEA model based on at least one structural crack prediction theory.

5. The method of claim 4, said conducting the steady-state dynamic (SSD) analysis and the vibro-acoustic analysis of the structure for obtaining the numerically-computed acoustic signatures at said various stages of the numerically-simulated crack propagation trajectory further comprises:
    obtaining, with the FEA application module, a structural surface nodal velocity distribution of the structure subject to the harmonic loading with the predefined magnitude at a predefined frequency acted on a sound generation location on the structure's surface via SSD analysis, wherein the structure is represented by the FEA model corresponding to each of the various stages of the numerically-simulated crack propagation trajectory; and
    obtaining, with the BEM application module, the numerically-computed acoustic signature of the structure at a sound receiving location using the structural surface nodal velocity distribution as a vibration boundary condition based on a vibro-acoustic computation theory.

6. The method of claim 5, wherein the crack propagation lengths correspond to said various stages of the numerical-simulated crack propagation trajectory.

7. The method of claim 5, wherein each of the at least one relationship in the database corresponds to a combination of the sound receiving location, the sound generation location and the predefined frequency of the harmonic loading.

8. The method of claim 7, wherein the measured and recorded acoustic signature comprises sound pressure in Pa (Pascals) or sound pressure level (SPL) in decibels (dB).

9. The method of claim 8, wherein the predefined magnitude and the predefined frequency of the harmonic loading cause the acoustic signature be recorded at least 30 dB of audible sound at the first location.

10. The method of claim 1, wherein the measured and recorded acoustic signature comprises audio file.

11. A system for determining an unknown length of crack propagation inside a structure, said system comprises:
an input/output (I/O) interface;
a memory for storing computer readable code for at least a finite element analysis (FEA) application module and a boundary element method (BEM) application module;
at least one processor coupled to the memory, said at least one processor executing the computer readable code in the memory to cause the application modules to perform operations of:
receiving a FEA model representing a structure and a loading condition known to cause a crack propagation in the structure;
obtaining, with the FEA application module, a numerically-simulated crack propagation trajectory within the structure under the loading condition by conducting the time-marching simulation using the FEA model based on at least one structural crack prediction theory;
obtaining, with the FEA application module, a structural surface nodal velocity distribution of the structure subject to a harmonic loading with a predefined magnitude at a predefined frequency acted on a sound generation location on the structure's surface via steady-state dynamic (SSD) analysis, wherein the structure is represented by the FEA model corresponding to each of various stages of the numerically-simulated crack propagation trajectory;
obtaining, with the BEM application module, a numerically-computed acoustic signature of the structure at a sound receiving location using the structural surface nodal velocity distribution as a vibration boundary condition based on a vibro-acoustic computation theory;
storing at least one relationship of respective numerically-computed acoustic signatures versus crack propagation lengths corresponding to said various stages of the numerically-simulated crack propagation trajectory in a database; and
determining an unknown length of crack propagation within the structure by comparing a measured and recorded acoustic signature with the numerically-computed acoustic signatures stored in the database, wherein the measured and recorded acoustic signature is obtained at a first location via an acoustic wave generated by vibrations of the structure caused by a harmonic loading with a predefined magnitude acted at a second location on the structure containing the unknown length of crack propagation inside.

12. The system of claim 11, wherein each of the at least one relationship in the database corresponds to a combination of the sound receiving location, the sound generation location and the predefined frequency of the harmonic loading.

13. The system of claim 12, wherein the measured and recorded acoustic signature comprises sound pressure in Pa (Pascals) or sound pressure level (SPL) in decibels (dB).

14. The system of claim 13, wherein the predefined magnitude and the predefined frequency of the harmonic loading cause the acoustic signature be recorded at least 30 dB of audible sound at the first location.

15. A non-transitory computer readable storage medium containing computer instructions for determining an unknown length of crack propagation inside a structure, said computer instructions when executed on a computer system cause the computer system to perform operations of:
receiving, in a computer system having at least a finite element analysis (FEA) application module and a boundary element method (BEM) application module installed thereon, a FEA model representing the structure and a loading condition known to cause a crack propagation in the structure;
obtaining, with the FEA application module, the numerically-simulated crack propagation trajectory within the structure under the loading condition by conducting the time-marching simulation using the FEA model based on at least one structural crack prediction theory;
obtaining, with the FEA application module, a structural surface nodal velocity distribution of the structure subject to a harmonic loading with a predefined magnitude at a predefined frequency acted on a sound generation location on the structure's surface via steady-state dynamic (SSD) analysis, wherein the structure is represented by the FEA model corresponding to each of various stages of the numerically-simulated crack propagation trajectory;
obtaining, with the BEM application module, a numerically-computed acoustic signature of the structure at a sound receiving location using the structural surface nodal velocity distribution as a vibration boundary condition based on a vibro-acoustic computation theory; and
storing at least one relationship of respective numerically-computed acoustic signatures versus crack propagation lengths corresponding to said various stages of the numerically-simulated crack propagation trajectory into the database; and
determining an unknown length of crack propagation within the structure by comparing a measured and recorded acoustic signature with the numerically-computed acoustic signatures stored in the database, wherein the measured and recorded acoustic signature is obtained at a first location via an acoustic wave generated by vibrations of the structure caused by a harmonic loading with a predefined magnitude acted at a second location on the structure containing the unknown length of crack propagation inside.

16. The non-transitory computer readable storage medium of claim 15, wherein each of the at least one relationship in the database corresponds to a combination of the sound receiving location, the sound generation location and the predefined frequency of the harmonic loading.

17. The non-transitory computer readable storage medium of claim 16, wherein the measured and recorded acoustic signature comprises sound pressure in Pa (Pascals) or sound pressure level (SPL) in decibels (dB).

18. The non-transitory computer readable storage medium of claim 17, wherein the predefined magnitude and the predefined frequency of the harmonic loading cause the acoustic signature be recorded at least 30 dB of audible sound at the first location.

* * * * *